United States Patent [19]

Mignani et al.

[11] Patent Number: 4,634,778

[45] Date of Patent: Jan. 6, 1987

[54] PROCESS FOR PREPARING CHLORINATED ETHYLENIC DERIVATIVES

[75] Inventors: Gerárd Mignani, Lyons; Didier Morel, Villiers sur Orge; Pierre Chabardès, Sainte Foy les Lyon, all of France

[73] Assignee: Rhone-Poulenc Sante, Courbevoie, France

[21] Appl. No.: 671,880

[22] Filed: Nov. 16, 1984

[30] Foreign Application Priority Data

Nov. 18, 1983 [FR] France ................................ 83 18390

[51] Int. Cl.[4] .......................................... C07D 333/48
[52] U.S. Cl. ...................................... 549/80; 549/408; 549/410; 560/219; 560/262; 568/393; 568/459; 568/596; 568/686; 568/849; 570/153; 570/234
[58] Field of Search ................ 570/234, 153; 549/398, 549/80, 408, 410; 560/214, 219, 262; 568/393, 459, 596, 686, 849

[56] References Cited

U.S. PATENT DOCUMENTS

| | | | |
|---|---|---|---|
| 2,189,890 | 5/1937 | Engs et al. ............................ | 570/234 |
| 2,777,883 | 1/1957 | Chambers et al. ................... | 570/234 |
| 2,783,285 | 2/1957 | Chambers et al. ................... | 570/234 |
| 2,995,600 | 8/1961 | Webb .................................. | 570/189 |
| 3,110,740 | 11/1963 | Peer et al. ........................... | 570/234 |
| 3,331,737 | 7/1967 | Wenham et al. .................... | 570/189 |
| 4,255,597 | 3/1981 | Paul et al. ........................... | 570/234 |
| 4,503,239 | 3/1985 | Desmurs ............................. | 568/459 |

FOREIGN PATENT DOCUMENTS 1034253  6/1966  United Kingdom .

OTHER PUBLICATIONS

Mathieu et al., *L'amenagement Fonctionnel en Synthese Organique*, Hermann (1977), pp. 241–244, 281–282, 237–239.

*Primary Examiner*—Natalie Trousof
*Assistant Examiner*—Bruce D. Gray
*Attorney, Agent, or Firm*—Stevens, Davis, Miller & Mosher

[57] ABSTRACT

Process for preparing chlorinated ethylenic derivatives of the formula

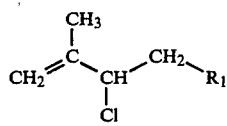
(I)

in which $R_1$ represents acetyl, formyl optionally in the form of an acetal, hydroxy optionally as an ether or ester, alkyloxycarbonyl, alkyl of 1 to 12 carbon atoms substituted by one or more acetyl, formyl optionally in the form of an acetal, hydroxy optionally in the form of an ether or ester, or alkyloxycarbonyl, alkenyl of 2 to 12 carbon atoms containing one or more double bonds optionally substituted by one or more of acetyl, formyl optionally in the form of an acetal, hydroxy optionally in the form of an ether or ester, or alkyloxycarbonyl, or $R_1$ represents 3-sulpholenyl or a radical of formula

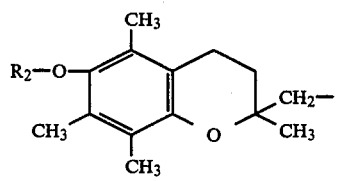
(II)

in which $R_2$ denotes a hydrogen or acetyl, by reacting chlorine in a nonpolar aprotic solvent with a compound of general formula

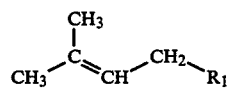
(III)

in which $R_1$ is defined as above. The products of formula I, some of which are new, are useful as intermediates in the synthesis of terpene products such as vitamin E.

4 Claims, No Drawings

PROCESS FOR PREPARING CHLORINATED ETHYLENIC DERIVATIVES

This invention relates to the preparation of chlorinated ethylenic derivatives and to new chlorinated derivatives so made.

It is known, for example from J. Mathieu et al. "L'aménagement fonctionnel en synthèse organique" (Functional arrangement in organic synthesis), Hermann (1977), p.237 and following, 242 and following, 281 and following, that, starting from molecules containing electron-attracting groups, such as a carbonyl group, or isolated or conjugated double bonds, halogenation with various halogenating agents results either in substitution in α-position relative to the electron-attracting group, or in addition to the double bonds.

It is also known to prepare selectively halogenated allyl derivatives from complex compounds, that is to say functional compounds or compounds incorporating several double bonds, by the action of hypochlorous acid, for example, on methyl γ-geranate, myrcene, citral in an enol form, or farnesol [cf. S. G. Hedge et al., Tetrahedron Letters, 21, 441 (1980) and S. G. Hedge et al., Tetrahedron, 22, 5019 (1981)] or by the action of gaseous chlorine in the presence of an inorganic base such as sodium carbonate or bicarbonate while operating in an organic solvent such as carbon tetrachloride (cf. for example U.S. Pat. No. 2,995,600).

However, these processes are difficult to use industrially and frequently require complex technology.

The present invention provides a new process for preparing chlorinated ethylenic derivatives of the formula:

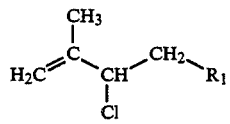

(I)

in which $R_1$ represents halogen; acetyl; formyl which may be in the form of an acetal radical; hydroxy which may be in the form of an ether or ester; an alkyloxycarbonyl radical whose alkyl part has 1 to 4 carbon atoms; an alkyl radical of from 1 to 12 carbon atoms and substituted by one or more identical or different radicals chosen from halogen, acetyl, formyl which may be in the form of an acetal radical, hydroxy which may be in the form of an ether or ester, or an alkyloxycarbonyl radical whose alkyl part has 1 to 4 carbon atoms; an alkenyl radical of 2 to 12 carbon atoms and one or more double bonds which is unsubstituted or substituted by one or more identical or different radicals chosen from halogen, acetyl, formyl which may be in the form of an acetal radical, hydroxy which may be in the form of an ether or ester, or an alkyloxycarbonyl radical whose alkyl part has 1 to 4 carbon atoms; or $R_1$ represents a 3-sulpholenyl radical or a radical or the formula:

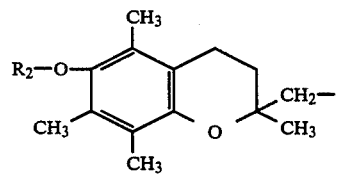

(II)

in which $R_2$ represents hydrogen or acetyl.

This new process comprises chlorinating a compound of the formula:

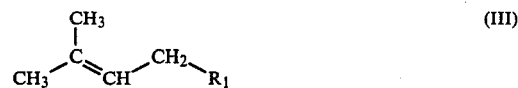

(III)

in which $R_1$ is as defined above, with chlorine, in a nonpolar aprotic organic solvent. This process produces selectively a compound of formula (I) whatever the identity of the radical $R_1$.

The use of the process according to the invention may consist in passing a stream of gaseous chlorine, if appropriate diluted with an inert carrier gas such as nitrogen or argon, into a solution of a compound of formula (III) in a suitable dry organic solvent.

It is possible to mention, as organic solvents which are particularly highly suitable, aliphatic saturated hydrocarbons, e.g. butane, pentane or hexane, halogenated aliphatic hydrocarbons, e.g. methylene chloride, cycloaliphatic hydrocarbons, e.g. cyclopentane or cyclohexane and aromatic hydrocarbons, e.g. benzene or toluene.

The process is generally carried out at a temperature of between −10° and 100° C., and preferably between 10° and 50° C. It is advantageous to operate at the boiling point of the solvent, under reduced pressure if appropriate. This operational procedure facilitates the removal of hydrochloric acid formed in the course of the reaction. It is also possible to distil the solvent off, while introducing fresh solvent in order to operate at constant volume, the recovered solvent being capable of being recycled into subsequent operations, after washing to remove hydrochloric acid and drying.

The concentration of the product of general formula (II) in the solvent is not critical and is generally 1 part by weight of product of general formula (II) per 1 to 4 parts of solvent.

The products of general formula (I) may be isolated from the reaction mixture after complete evaporation of the solvent, and washed, if appropriate, to remove the hydrochloric acid formed.

The products of general formula (I) obtained in this way may be purified by application of conventional methods such as crystallisation, distillation or chromatography.

The products of general formula (I) in which $R_1$ denotes a two-oxo-1-carbomethoxypropyl, 6-oxo-2-methyl-2-heptenyl, 6-oxo-5-carbomethoxy-2-methyl-2-heptenyl, 6-oxo-2-methyleneheptyl, 6-oxo-2-methylene-5-carbomethoxyheptyl, 2,6-dimethyl-10-oxo-2,6-undecadienyl, 2,6-dimethyl-9-carbomethoxy-10-oxo-2,6-undecadienyl, 2-methyl-6-methylene-10-oxo-2-undecenyl or 2-methyl-6-methylene-9-carbomethoxy-10-oxo-2-undecenyl radical, if appropriate in the form of acetal, are new products which form another subject of the present invention.

The process according to the present invention makes it possible to obtain products of general formula (I) with yields which are generally above 70% by the use of industrial techniques which are simpler than those required for implementing previously known processes.

The products obtained according to the process of the present invention form intermediates which are particularly useful for the preparation of terpene products such as vitamin E. Those of very particular interest are 3-chloromethylheptenone(3-chloro-2-methyl-1-hepten-6one), 3-chlorogeranylacetone(2,6-dimethyl-3-chloro-1,6-undecadien-10-one), 3-chlorofarnesylacetone(2,6,10-trimethyl-3-chloro-1,6,10-pentadecatrien-14-one) and 3-chloromyrcene(3-chloro-2-methyl-6-methylene-1,7-octadiene).

The following examples illustrate the invention.

EXAMPLE 1

Into a 500 cc round flask are introduced, under an argon atmosphere, geranylacetone (58.96 g), a cis-trans mixture of

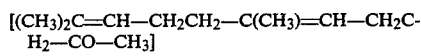

[(CH$_3$)$_2$C=CH—CH$_2$CH$_2$—C(CH$_3$)=CH—CH$_2$CH$_2$—CO—CH$_3$]

(i.e. 0.3031 mole) and dry pentane (200 cc). The mixture is heated to reflux and into this solution gaseous chlorine (21.5 g; 0.3 mole) is then added over 1 hour 50 minutes. After evaporation of the solvent, a yellow oil (75.08 g) is obtained which, after distillation at 119°–124° C. under a pressure of 0.02 kPa, yields 3-chlorogeranylacetone (35.98 g; 0.157 mole) of formula:

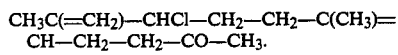

CH$_3$C(=CH$_2$)—CHCl—CH$_2$—CH$_2$—C(CH$_3$)=CH—CH$_2$—CH$_2$—CO—CH$_3$.

The yield of isolated product is 51.8% based on the geranylacetone employed.

Gas phase chromatographic analysis of the crude product of the reaction shows that:
the degree of conversion of geranylacetone is 88.5%
the yield of 3-chlorogeranylacetone is 64.9% based on the geranylacetone employed
the yield of 3-chlorogeranylacetone is 73.3% based on the geranylacetone converted.

The structure of the product obtained is confirmed by the infrared spectrum and the mass spectrum. The proton nuclear magnetic resonance spectrum shows that the product obtained consists of 60% of trans isomer and 40% of cis isomer.

EXAMPLE 2

Into a 500 cc three-necked round flask are added, under an argon atmosphere, an equimolar mixture (25 g; 128.8 millimoles) of the two isomeric products of formulae:

(CH$_3$)$_2$C=CH—CH$_2$CH$_2$—C(CH$_3$)=CH—CH$_2$CH$_2$—CO—CH$_3$ and (CH$_3$)$_2$C=CH—CH$_2$CH$_2$—(=CH$_2$)—CH$_2$CH$_2$CH$_2$COCH$_3$ and dry pentane (100 cc). The mixture is heated to reflux and then gaseous chlorine (8.87 g; 125 millimoles) is added over 1 hour. After evaporation of the solvent, a yellow oil (32.54 g) is obtained which, after distillation at 121°–126° C. under a pressure of 0.02 kPa yields a 25–75 mixture (17.5 g; 76 millimoles) of the products of formulae:

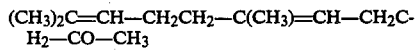

CH$_2$=C(CH$_3$)—CHCl—CH$_2$CH$_2$—C(CH$_3$)=CH—CH$_2$CH$_2$COCH$_3$ and

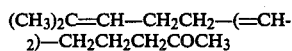

CH$_2$=C(CH$_3$)—CHCl—CH$_2$CH$_2$C(=CH$_2$)—CH$_2$CH$_2$CH$_2$COCH$_3$.

The yield of isolated product is 59.5% based on the products employed.

Gas phase chromatographic analysis of the crude product of the reaction shows that:
the degree of conversion of the products employed is 95.7%
the yield is 60.6% based on the products employed
the yield is 63.3% based on the employed products converted.

The products obtained are characterised by the infrared spectrum, mass spectrum and proton nuclear magnetic resonance spectrum.

EXAMPLE 3 (comparative test)

Into a 500 cc three-necked round flask are introduced, under an argon atmosphere, geranylacetone (cis-trans mixture) (53.74 g; 0.277 mole), dry pentane (200 cc) and sodium carbonate (30 g; 0.283 mole). The mixture is heated to reflux and then gaseous chlorine (19.6 g; 0.277 mole) is added over 1 hour 30 minutes. After cooling, the reaction mixture is filtered and then washed with water until neutral. The organic phases are dried. After being filtered on filter paper (Whatman paper) the solvent is evaporated off. In this way a yellow oil (67.07 g) is obtained which, after being distilled under reduced pressure, yields a cis-trans mixture (23.4 g; 0.102 mole) of product of formula:

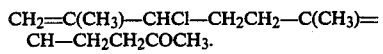

CH$_2$=C(CH$_3$)—CHCl—CH$_2$CH$_2$—C(CH$_3$)=CH—CH$_2$CH$_2$COCH$_3$.

The yield of isolated product is 37% based on the geranylacetone employed.

Gas phase chromatographic analysis of the crude reaction product shows that:
the degree of conversion of geranylacetone is 88.6%
the yield of 3-chlorogeranylacetone is 40.1% based on the geranylacetone employed
the yield of 3-chlorogeranylacetone is 45.2% based on the geranylacetone converted.

The structure of the product obtained is confirmed by the infrared spectrum, mass spectrum and proton nuclear magnetic resonance spectrum.

EXAMPLE 4

Into a 500 cc three-necked round flask are introduced, under an argon atmosphere, methylheptenone (38 g; 0.3 mole)

[(CH$_3$)$_2$C=CH—CH$_2$CH$_2$—CO—CH$_3$]

and dry pentane (200 cc). The mixture is heated to reflux and then gaseous chlorine (21.3 g; 0.3 mole) is added over 1 hour 30 minutes. After cooling, the solvent is evaporated off. A yellow oil (52.74 g) is obtained which, after distillation at 58° C. under reduced pressure (0.17 kPa), yields a mixture (42.46 g) containing 35% of 3-chloromethylheptenone, as estimated from the proton nuclear magnetic resonance spectrum.

The degree of conversion of 6-methyl-5-hepten-2-one is 75%.

The yield of 3-chloro-2-methyl-1-hepten-6-one is 35% based on the methylheptenone employed. The selectivity is 46.6%.

The structure of the product obtained is confirmed by the infrared spectrum, mass spectrum and proton nuclear magnetic resonance spectrum.

EXAMPLE 5

Into a 500 cc three-necked round flask are introduced, under an argon atmosphere:

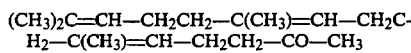

(77.84 g; 0.297 mole) and dry pentane (200 cc). The mixture is heated to reflux and then gaseous chlorine (21.3 g; 0.3 mole) is introduced over 1 hour 30 minutes. After evaporation of the solvent, a yellow oil (89.20 g) is recovered which, after distillation at 170°–175° C. under reduced pressure (0.053 kPa), yields product of formula:

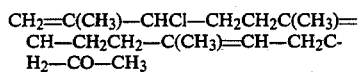

(30 g; 0.101 mole) with a yield of 34.1% based on the product employed.

The structure of the product obtained is confirmed by the mass spectrum and the infrared spectrum.

EXAMPLE 6

Into a 1 liter three-necked round flask are introduced, under an argon atmosphere, distilled myrcene (42 g; 0.3088 mole) and dry hexane (104 cc). The mixture is heated to 65° C., and then gaseous chlorine (21.6 g; 0.3088 mole) is introduced over 2 hours 30 minutes while the hexane (400 cc) is distilled off, the distilled hexane being compensated by the addition of hexane (400 cc) during distillation. After evaporation of the solvent under reduced pressure (2.7 kPa), a yellow oil (54.52 g) is obtained, the analysis of which by gas phase chromatography shows that it contains 71.3% of 3-chloromyrcene and 10.1% of unreacted myrcene.

The degree of conversion of myrcene is 86.8%.

The yield is 63.5% based on the myrcene employed and 73.2% based on the converted myrcene.

EXAMPLE 7

Into a 500 cc three-necked round flask are introduced, under an argon atmosphere, a cis-trans mixture (25 g) of

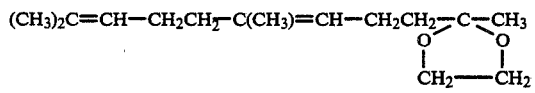

analysing at 85% i.e. 89.3 millimoles and pentane (100 cc). The mixture is heated to reflux and then gaseous chlorine (89.3 millimoles) are introduced over 30 minutes. After evaporation of the solvent, a yellow oil (29.2 g) is obtained which, after distillation at 135° C. under a pressure of 0.12 kPa, yields a cis-trans mixture (17.68 g; 64.8 millimoles) of product of formula:

The yield of isolated product is 72.6% based on the acetal employed.

The structure of the product obtained is confirmed by the infrared spectrum, the mass spectrum and the proton nuclear magnetic resonance spectrum.

EXAMPLE 8

Into a 500 cc three-necked round flask are introduced, under an argon atmosphere, a mixture (28.21 g; 112 millimoles) consisting of the products:

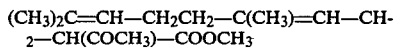

and

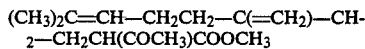

and dry pentane (100 cc). The mixture is heated to reflux and then gaseous chlorine (112 millimoles) is introduced over 1 hour 30 minutes. After evaporation of the solvent, a light yellow oil (33.62 g) is obtained which, after distillation at 146° C. under 0.11 kPa yields a mixture (27.86 g; 97.2 millimoles) of products of formula:

and

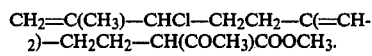

The degree of conversion of the products employed is 100%.

The yield is 86.7% relative to the products employed.

EXAMPLE 9

A 4-liter reactor is employed, fitted with mechanical stirring, a thermometer, a device for bubbling gas, a pentane inlet (controlled by a pump), a distillation column the outlet of which is connected to a 5-liter round flask containing 1.5N caustic soda which is circulated by means of a pump downwards through a column packed with Raschig rings mounted above the round flask (in order to remove the hydrochloric acid carried off by the pentane), and itself connected to a round flask in which the pentane is condensed.

Into the reactor are introduced, under an argon atmosphere, pure myrcene (840 g; 6.176 moles) and pentane (2 liters). The round flask is heated by means of a bath at 45°–55° C. The temperature of the reaction mixture is 35° C. A gaseous mixture of chlorine and argon is then led in, the ratio of the flow rates of chlorine and argon being 7/12. The pentane and the hydrochloric acid formed are removed by distillation while pentane is simultaneously added in order to maintain a constant volume. The rate of addition of chlorine is 167 g/hour and that of pentane 2 liters/hour. After 2 hours 40 minutes 440 g (6.19 moles) of chlorine and 5 liters of pentane have been added. The volume of the pentane col-

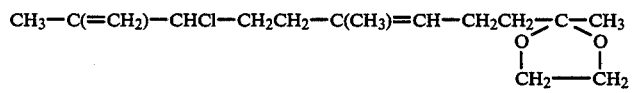

lected is 5.5 liters. After the chlorine addition has ended, the pentane present in the reactor is removed by distillation at 40° C. under 5.3 kPa. A residue weighing 1,080 g is obtained in this way and is rapidly distilled between 34° and 60° C. under 0.08 kPa. The distillate obtained (1,026 g) analyses at 86.9% 3-chloromyrcene. The yield is 84.6% based on the myrcene employed.

Analysis for myrcene in the light distillates shows that the degree of conversion is 96.4%.

The yield is 87.8% based on the reacted myrcene.

EXAMPLE 10

Into a 1 liter three-necked round flask are introduced, under an argon atmosphere, linalol (77.42 g; 0.5 mole) of formula $$(CH_3)_2CH=CH-CH_2CH_2-C(CH_3)(OH)-CH=CH_2,$$

and dry pentane (600 cc). The mixture is heated to reflux and then gaseous chlorine (35.5 g; 0.5 mole) is introduced over 2 hours.

After evaporation of the solvent, a colourless oil (97.74 g) is recovered, containing the product of the formula $$\underset{\underset{}{}}{CH_2}=\underset{\underset{}{CH_3}}{C}-CHCl-CH_2CH_2-\underset{\underset{OH}{}}{\overset{CH_3}{C}}-CH=CH_2$$

This product is obtained in a yield of 55% based on the linalol employed.

EXAMPLE 11

Into a 500 cc round flask are introduced, under an argon atmosphere, methylene chloride (250 cc) and 2,5,7,8-tetramethyl-2-(4-methyl-3-pentenyl)-6-chromanol (7.9 g) analysing at 90%, i.e. 24.68 millimoles. The mixture is heated to reflux and then gaseous chlorine (2 g; 28.16 millimoles) is introduced over 1 hour. After evaporation of the solvent, a slightly yellow oil (8.62 g) is obtained the analysis of which by liquid phase chromatography shows that it contains 57.7% of 2,5,7,8-tetramethyl-2-(3-chloro-4-methyl-4-pentenyl)-6-chromanol.

The degree of conversion of the starting product is 71%. The yield is 81% based on the starting product converted.

The structure of the product obtained is confirmed by the infrared spectrum, the mass spectrum and the proton nuclear magnetic resonance spectrum.

EXAMPLE 12

Into a 250 cc three-necked reactor, fitted with mechanical stirring, an immersed gas inlet, a dropping funnel, a device for removing gases and trapping the distilled pentane, are introduced linalyl acetate (29.4 g; 0.15 mole) and dry pentane (60 cc). The mixture is heated to 36° C. and then gaseous chlorine, diluted with argon, is introduced, the distilled pentane being replaced with fresh pentane so as to keep the level constant in the reactor. After 2 hours 18 minutes 300 cc of pentane have been distilled and added and 11.3 g (0.159 mole) of chlorine have been added. After evaporation of the solvent under reduced pressure (20 mm Hg; 2.7 kPa) a slightly yellow oil (34.5 g) is obtained.

Analysis by gas phase chromatography shows that the oil obtained contains 86% of 6-acetoxy-3-chloro-2,6-dimethyl-1,7-octadiene.

The degree of conversion of the linalyl acetate is 100%.

The structure of the product obtained is confirmed by the proton nuclear magnetic resonance spectrum which shows the presence of an equimolecular mixture of the two diastereoisomers.

EXAMPLE 13

The procedure employs an apparatus identical to that described in Example 12. Geranyl chloride (25.9 g; 0.15 mole) and dry pentane (60 cc) are introduced. The reaction mixture is heated to 37° C. and then gaseous chlorine diluted with argon is introduced, the distilled pentane being replaced with fresh pentane so as to keep the level constant in the reactor. After 3 hours 360 cc of pentane have been distilled and added and 10.6 g (0.15 mole) of chlorine have been added. After evaporation of the solvent a crude product (30.6 g) is obtained which is rapidly distilled at 95° C. under reduced pressure (0.5 mm Hg; 0.067 kPa).

Analysis of the distillate by gas phase chromatography and by proton nuclear magnetic resonance spectrum shows that the degree of conversion of the geranyl chloride is 65% and that 3,8-dichloro-2,6-dimethyl-1,6-octadiene is obtained in a yield of 91% based on the converted geranyl chloride.

We claim:

1. A process for preparing a chlorinated ethylenic derivative of the formula:

$$CH_2=\underset{\underset{}{}}{\overset{CH_3}{C}}\diagdown\underset{\underset{Cl}{}}{CH}\diagdown CH_2\diagdown R_1$$

in which $R_1$ represents halogen; acetyl; formyl which may be in the form of an acetal radical; hydroxy which may be in the form of an ether or ester; an alkyloxycarbonyl radical whose alkyl part has 1 to 4 carbon atoms; an alkyl radical of from 1 to 12 carbon atoms and substituted by one or more identical or different radicals chosen from halogen, acetyl, formyl which may be in the form of an acetal radical, hydroxy which may be in the form of an ether or ester, or an alkyloxycarbonyl radical whose alkyl part has 1 to 4 carbon atoms; an alkenyl radical of 2 to 12 carbon atoms and one or more double bonds which is unsubstituted or substituted by one or more identical or different radicals chosen from halogen, acetyl, formyl which may be in the form of an acetal radical, hydroxy which may be in the form of an ether or ester, or an alkyloxycarbonyl radical whose alkyl part has 1 to 4 carbon atoms; or $R_1$ represents a 3-sulpholenyl radical or a radical of the formula:

in which $R_2$ is hydrogen or acetyl, which process comprises chlorinating a compound of the formula:

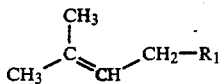

with chlorine in a nonpolar aprotic organic solvent at a temperature of between −10° and 100° C.

2. A process according to claim 1, in which the solvent is a saturated aliphatic hydrocarbon, halogenated aliphatic hydrocarbon, cycloaliphatic hydrocarbon, or aromatic hydrocarbon.

3. A process according to claim 1, in which the chlorination is effected at the reflux temperature of the reaction mixture, under reduced or ambient pressure.

4. A process according to claim 1, in which the solvent is distilled off in an operation at constant volume.

* * * * *